(12) United States Patent
Zhu et al.

(10) Patent No.: US 10,207,109 B2
(45) Date of Patent: *Feb. 19, 2019

(54) SYSTEM FOR COMBINING ELECTRICAL WAVEFORMS INTO A COMBINED ELECTRICAL WAVEFORM

(71) Applicant: Boston Scientific Neuromodulation Corporation, Valencia, CA (US)

(72) Inventors: Changfang Zhu, Valencia, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/145,425

(22) Filed: May 3, 2016

(65) Prior Publication Data

US 2016/0243366 A1    Aug. 25, 2016

Related U.S. Application Data

(63) Continuation of application No. 14/186,927, filed on Feb. 21, 2014, now Pat. No. 9,358,391.
(Continued)

(51) Int. Cl.
*A61N 1/36*       (2006.01)

(52) U.S. Cl.
CPC ..... *A61N 1/36071* (2013.01); *A61N 1/36146* (2013.01); *A61N 1/36178* (2013.01); *A61N 1/36167* (2013.01)

(58) Field of Classification Search
CPC .............. A61N 1/36071; A61N 1/36146
See application file for complete search history.

(56) References Cited

U.S. PATENT DOCUMENTS 4,398,537 A    8/1983  Holmbo
4,592,359 A    6/1986  Galbraith
(Continued)

FOREIGN PATENT DOCUMENTS

CN    101610735 A    12/2009
CN    101687093 A    3/2010
(Continued)

OTHER PUBLICATIONS

"U.S. Appl. No. 14/186,927, Final Office Action dated Nov. 20, 2015", 5 pgs.
(Continued)

*Primary Examiner* — Carl H Layno
*Assistant Examiner* — Jennifer Ghand

(57) ABSTRACT

A neuromodulation system comprises electrical terminals configured for being respectively coupled to electrodes. The system further comprises modulation output circuitry configured for respectively outputting individual electrical pulse trains in timing channels to the electrical terminals, wherein each of the pulse trains has a modulation pulse, and at least one of the pulse trains has a charge recovery pulse associated with the modulation pulse of the respective pulse train. The neuromodulation system further comprises control circuitry configured for controlling the modulation output circuitry in a manner that sequentially outputs the modulation pulses of the respective pulse trains to a common set of the electrical terminals without an intervening charge recovery pulse, and outputting the charge recovery pulse(s) to the common set of the electrical terminals subsequent to the sequential modulation pulses, thereby creating a combined electrical pulse train at the common set of electrical terminals.

20 Claims, 8 Drawing Sheets

Related U.S. Application Data

(60) Provisional application No. 61/768,305, filed on Feb. 22, 2013.

(56) References Cited

U.S. PATENT DOCUMENTS

| | | | |
|---|---|---|---|
| 5,603,726 | A | 2/1997 | Schulman et al. |
| 6,289,247 | B1 | 9/2001 | Faltys et al. |
| 6,516,227 | B1 | 2/2003 | Meadows et al. |
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 8,019,439 | B2 | 9/2011 | Kuzma et al. |
| 8,170,675 | B2 | 5/2012 | Alataris et al. |
| 8,209,021 | B2 | 6/2012 | Alataris et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,359,102 | B2 | 1/2013 | Alataris et al. |
| 8,359,103 | B2 | 1/2013 | Alataris et al. |
| 8,396,559 | B2 | 3/2013 | Alataris et al. |
| 8,423,147 | B2 | 4/2013 | Alataris et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,731,675 | B2 | 5/2014 | Ranu et al. |
| 8,751,009 | B2 | 6/2014 | Wacnik |
| 9,339,655 | B2 | 5/2016 | Carbunaru |
| 9,358,391 | B2 * | 6/2016 | Zhu .................... A61N 1/36146 |
| 9,724,513 | B2 | 8/2017 | Lane et al. |
| 2003/0139781 | A1 | 7/2003 | Bradley et al. |
| 2004/0034394 | A1 | 2/2004 | Woods et al. |
| 2005/0267546 | A1 | 12/2005 | Parramon et al. |
| 2006/0149337 | A1 | 7/2006 | John |
| 2007/0142874 | A1 | 6/2007 | John |
| 2007/0150036 | A1 | 6/2007 | Anderson |
| 2007/0168004 | A1 | 7/2007 | Walter |
| 2007/0168007 | A1 | 7/2007 | Kuzma et al. |
| 2007/0225765 | A1 | 9/2007 | King |
| 2008/0188909 | A1 | 8/2008 | Bradley |
| 2009/0204173 | A1 | 8/2009 | Fang et al. |
| 2010/0010566 | A1 | 1/2010 | Thacker et al. |
| 2010/0023090 | A1 | 1/2010 | Jaax et al. |
| 2010/0114196 | A1 | 5/2010 | Burnes et al. |
| 2010/0121409 | A1 | 5/2010 | Kothandaraman et al. |
| 2010/0152817 | A1 * | 6/2010 | Gillbe ................... A61N 1/0551 607/72 |
| 2010/0249875 | A1 | 9/2010 | Kishawi et al. |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274316 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2010/0324630 | A1 | 12/2010 | Lee et al. |
| 2011/0040352 | A1 | 2/2011 | Gerber et al. |
| 2011/0054567 | A1 * | 3/2011 | Lane .................... A61N 1/08 607/59 |
| 2011/0106214 | A1 * | 5/2011 | Carbunaru .......... A61N 1/36128 607/60 |
| 2011/0125223 | A1 | 5/2011 | Carbunaru et al. |
| 2011/0160810 | A1 * | 6/2011 | Griffith ................ A61N 1/0531 607/72 |
| 2011/0184486 | A1 | 7/2011 | De Ridder |
| 2011/0184488 | A1 | 7/2011 | De Ridder |
| 2011/0201977 | A1 | 8/2011 | Tass |
| 2012/0016437 | A1 | 1/2012 | Alataris et al. |
| 2012/0059446 | A1 | 3/2012 | Wallace et al. |
| 2012/0083709 | A1 | 4/2012 | Parker et al. |
| 2012/0203304 | A1 | 8/2012 | Alataris et al. |
| 2012/0253422 | A1 | 10/2012 | Thacker et al. |
| 2012/0265279 | A1 | 10/2012 | Zhu et al. |
| 2012/0283797 | A1 | 11/2012 | De Ridder |
| 2012/0290041 | A1 | 11/2012 | Kim et al. |
| 2013/0041425 | A1 | 2/2013 | Fang et al. |
| 2013/0066411 | A1 | 3/2013 | Thacker et al. |
| 2013/0116752 | A1 | 5/2013 | Parker et al. |
| 2013/0131760 | A1 | 5/2013 | Rao et al. |
| 2013/0268021 | A1 | 10/2013 | Moffitt |
| 2013/0296975 | A1 | 11/2013 | Lee et al. |
| 2014/0005753 | A1 * | 1/2014 | Carbunaru .......... A61N 1/36189 607/62 |
| 2014/0081349 | A1 | 3/2014 | Lee et al. |
| 2014/0243924 | A1 | 8/2014 | Zhu et al. |
| 2014/0277267 | A1 | 9/2014 | Vansickle et al. |
| 2014/0330345 | A1 | 11/2014 | John |
| 2014/0364920 | A1 | 12/2014 | Doan et al. |
| 2016/0250472 | A1 | 9/2016 | Carbunaru |
| 2017/0326365 | A1 | 11/2017 | Lane et al. |

FOREIGN PATENT DOCUMENTS

| | | |
|---|---|---|
| CN | 105188838 B | 4/2017 |
| GB | 2449546 A | 11/2008 |
| JP | 2004181100 A | 7/2004 |
| JP | 2006116332 A | 5/2006 |
| JP | 2010523215 A | 7/2010 |
| JP | 2010527675 A | 8/2010 |
| JP | 2015521532 A | 7/2015 |
| JP | 2016507335 A | 3/2016 |
| JP | 6163549 B2 | 6/2017 |
| WO | WO-2006029257 A2 | 3/2006 |
| WO | WO-2006135791 A2 | 12/2006 |
| WO | WO-2008095185 A1 | 8/2008 |
| WO | WO-2014130865 | 8/2014 |
| WO | WO-2014197596 A1 | 12/2014 |

OTHER PUBLICATIONS

"U.S. Appl. No. 14/186,927, Non Final Office Action dated May 5, 2015", 7 pgs.

"U.S. Appl. No. 14/186,927, Response filed Jan. 20, 2016 to Final Office Action dated Nov. 20, 2015", 8 pgs.

"U.S. Appl. No. 14/186,927, Response filed Aug. 4, 2015 to Non Final Office Action dated May 5, 2015", 10 pgs.

"U.S. Appl. No. 14/186,927, Notice of Allowance dated Feb. 10, 2016", 8 pgs.

"International Application Serial No. PCT/US2014/017789, International Search Report dated May 22, 2014", 3 pgs.

"International Application Serial No. PCT/US2014/017789, Written Opinion dated May 22, 2014", 5 pgs.

"U.S. Appl. No. 15/149,662, Non Final Office Action dated Apr. 19, 2017", 11 pgs.

"U.S. Appl. No. 15/149,662, Response filed Aug. 21, 2017 to Non Final Office Action dated Apr. 19, 2017", 14 pgs.

"U.S. Appl. No. 15/667,891, Preliminary Amendment filed Aug. 11, 2017", 7 pgs.

"Australian Application Serial No. 2014218716, First Examiners Report dated Aug. 4, 2017", 2 pgs.

"Australian Application Serial No. 2014218716, Response filed Sep. 6, 2017 to First Examiners Report dated Aug. 4, 2017", 8 pgs.

"European Application Serial No. 13739318.7, Communication Pursuant to Article 94(3) EPC dated Apr. 6, 2017", 4 pgs.

"European Application Serial No. 13739318.7, Response filed Aug. 9, 2017 to Communication Pursuant to Article 94(3) EPC dated Apr. 6, 2017", 7 pgs.

"U.S. Appl. No. 15/149,662, Advisory Action dated Jan. 29, 2018", 3 pgs.

"U.S. Appl. No. 15/149,662, Final Office Action dated Nov. 24, 2017", 11 pgs.

(56) References Cited

OTHER PUBLICATIONS

"U.S. Appl. No. 15/149,662, Response filed Jan. 16, 2018 to Final Office Action dated Nov. 24, 2017", 19 pgs.
"Japanese Application Serial No. 2015-559013, Office Action dated Dec. 11, 2017", w/ English translation, 5 pgs.

* cited by examiner

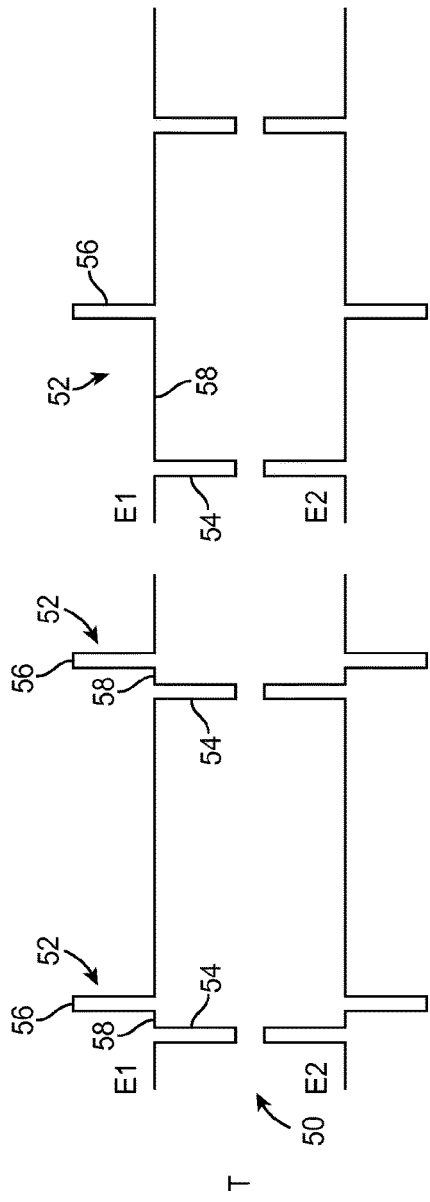
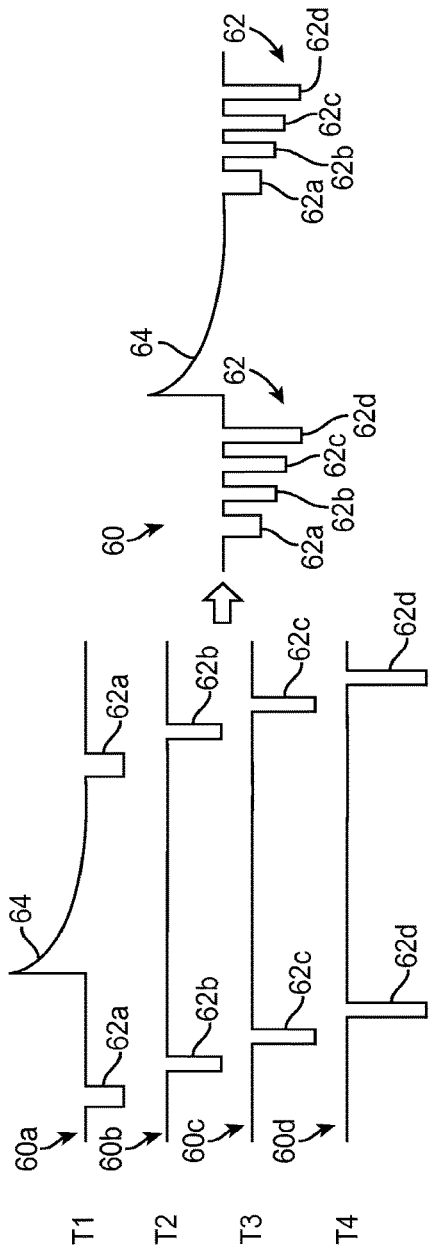
FIG. 6a
FIG. 6b
FIG. 7

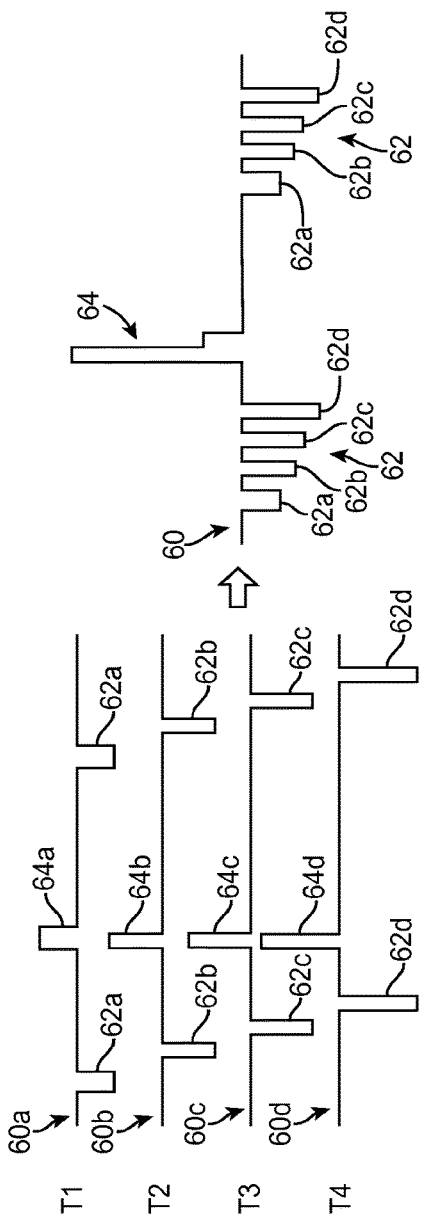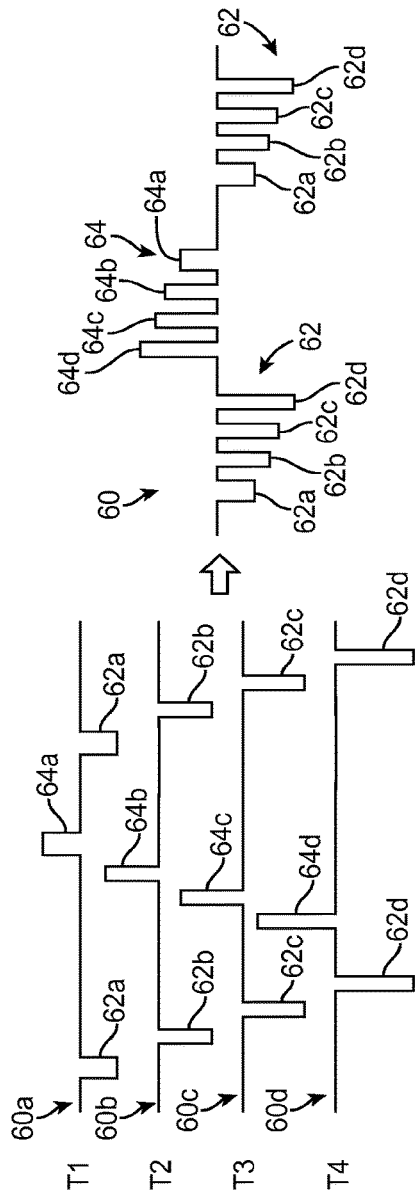
FIG. 8
FIG. 9

SYSTEM FOR COMBINING ELECTRICAL WAVEFORMS INTO A COMBINED ELECTRICAL WAVEFORM

RELATED APPLICATION DATA

The present application is a continuation of U.S. application Ser. No. 14/186,927, filed Feb. 21, 2014, now issued as U.S. Pat. No. 9,358,391, which claims the benefit under 35 U.S.C. § 119 to U.S. provisional patent application Ser. No. 61/768,305, filed Feb. 22, 2013. The foregoing applications are hereby incorporated by reference into the present application in their entirety.

FIELD OF THE INVENTION

The present invention relates to tissue stimulation systems, and more particularly, to a system and method for delivering complex electrical pulse trains using multi-channel neurostimulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying modulation leads, which are implanted at the desired stimulation site, and a neuromodulator (e.g., an implantable pulse generator (IPG)) implanted remotely from the stimulation site, but coupled either directly to the modulation lead(s) or indirectly to the modulation lead(s) via a lead extension. The neuromodulation system may further comprise an external control device to remotely instruct the neuromodulator to generate electrical modulation pulses in accordance with selected modulation parameters.

Electrical modulation energy may be delivered from the neuromodulator to the electrodes in the form of a pulsed electrical waveform. Thus, modulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, duration, and rate of the electrical pulses provided through the electrode array. Each electrode combination, along with the electrical pulse parameters, can be referred to as a "modulation parameter set."

With some neuromodulation systems, and in particular, those with independently controlled current or voltage sources, the distribution of the current to the electrodes (including the case of the neuromodulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulator to generate electrical modulation pulses in accordance with the selected modulation parameters. Typically, the modulation parameters programmed into the neuromodulator can be adjusted by manipulating controls on the external control device to modify the electrical stimulation provided by the neuromodulator system to the patient. However, the number of electrodes available combined with the ability to generate a variety of complex modulation pulses, presents a vast selection of modulation parameter sets to the clinician or patient.

To facilitate such selection, the clinician generally programs the neuromodulator through a computerized programming system. This programming system can be a self-contained hardware/software system, or can be defined predominantly by software running on a standard personal computer (PC). The PC or custom hardware may actively control the characteristics of the electrical stimulation generated by the neuromodulator to allow the optimum modulation parameters to be determined based on patient feedback or other means and to subsequently program the neuromodulator with the optimum modulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Often, multiple timing channels are used when applying electrical stimulation to target different tissue regions in a patient. For example, in the context of SCS, the patient may simultaneously experience pain in different regions (such as the lower back, left arm, and right leg) that would require the electrical stimulation of different spinal cord tissue regions. In the context of DBS, a multitude of brain structures may need to be electrically stimulated in order to simultaneously treat ailments associated with these brain structures. Each timing channel identifies the combination of electrodes used to deliver electrical pulses to the targeted tissue, as well as the characteristics of the current (pulse amplitude, pulse duration, pulse frequency, etc.) flowing through the electrodes.

The electrical modulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) charge recovery phase that is generated after the stimulation phase to prevent direct current charge transfer through the tissue, thereby avoiding cell trauma and electrode degradation via corrosion. That is, charge is conveyed through the electrode-tissue interface via current at an electrode during a stimulation period (the length of the modulation pulse), and then pulled back off the electrode-tissue interface via an oppositely polarized current at the same electrode during a recharge period (the length of the recharge pulse). Each biphasic pulse has an interphase that defined the time period between the stimulation phase and the charge recovery phase.

In the context of an SCS procedure, one or more leads are introduced through the patient's back into the epidural space, such that the electrodes carried by the leads are arranged in a desired pattern and spacing to create an electrode array. After proper placement of the leads at the target area of the spinal cord, the leads are anchored in place at an exit site to prevent movement of the leads. To facilitate the location of the neuromodulator away from the exit point of the leads, lead extensions are sometimes used. The leads, or the lead extensions, are then connected to the IPG, which can then be operated to generate electrical pulses that are delivered, through the electrodes, to the targeted spinal cord tissue. The modulation, and in the conventional case, the stimulation, creates the sensation known as paresthesia, which can be characterized as an alternative sensation that replaces the pain signals sensed by the patient. The efficacy of SCS is related to the ability to modulate the spinal cord tissue corresponding to evoked paresthesia in the region of the body where the patient experiences pain. Thus, the working clinical paradigm is that achievement of an effective result from SCS depends on the modulation lead or leads being placed in a location (both longitudinal and lateral) relative to the spinal tissue such that the electrical modulation will induce paresthesia located in approximately the same place in the patient's body as the pain (i.e., the target of treatment).

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. In contrast to conventional neuromodulation therapies, which employ low- to mid-frequencies to efficiently induce desired firing rate of action potentials from electrical pulses (e.g., one pulse can induce a burst of action potentials, or multiple pulses may be temporally integrated to induce on action potential), high frequency modulation (e.g., 1 KHz-50 KHz) can be employed to block or otherwise disrupt naturally occurring action potentials within neural fibers or otherwise disrupt the action potentials within the neural fibers. Although high-frequency modulation therapies have shown good efficacy in early studies, it would be desirable to provide high-frequency modulation therapy.

Once programmed, current neuromodulation systems are designed to deliver tonic modulation pulse trains in each timing channel (i.e., the pulse amplitude, pulse rate, pulse width, and interphase) are fixed. As a result, current neuromodulation systems are only capable of generating a simple pulse train for each of the timing channels. However, in some cases, it may be desirable to generate more complex pulse trains, which may be useful in controlling the response in neurons. For example, neuron response is a dynamic time course that can vary with sequential modulation. It is hypothesized that there is a temporal integration of the modulation effects induced from multiple pulses if the train of pulses is programmed within the responsive time frame of neuron. It would, thus, be desirable to provide therapy using complex pulse trains.

While neuromodulation systems can be designed with hardware capable of generating complex and/or high frequency pulse trains, redesigning the hardware on presently existing neuromodulation designs to accommodate these pulse trains may be a monumental task. Furthermore, neuromodulation systems that are currently used in the field may not be easily updated to generate these pulse trains.

There, thus, remains a need to provide an improved technique for more easily enabling presently existing neuromodulation systems to generate more complex and/or higher frequency pulse trains.

SUMMARY OF THE INVENTION

In accordance with the present inventions, a neuromodulation system comprises a plurality of electrical terminals configured for being respectively coupled to a plurality of electrodes, and modulation output circuitry configured for respectively outputting a plurality of individual electrical pulse trains in a plurality of timing channels to the plurality of electrical terminals. Each of the pulse trains has a modulation pulse, and at least one of the pulse trains has a charge recovery pulse associated with the modulation pulse of the at least one respective pulse train. In one embodiment, the modulation pulses have the same pulse amplitude and the same pulse width. In another embodiment, at least two of the modulation pulses have at least one of a different pulse amplitude and a different pulse width. The charge recovery pulse may be either passive or active.

The neuromodulation system further comprises control circuitry configured for controlling the modulation output circuitry in a manner that sequentially outputs the modulation pulses of the respective pulse trains to a common set of the electrical terminals (which may include only one electrical terminal or more than one electrical terminal) without an intervening charge recovery pulse, and outputting the charge recovery pulse of the at least one pulse train to the common set of the electrical terminals subsequent to the sequential modulation pulses, thereby creating a combined electrical pulse train at the common set of electrical terminals.

The sequential modulation pulses may be temporarily spaced apart relative to each other, which may be uniform. The sequential modulation pulses may be temporarily spaced apart relative to each other by a time period less than 1 ms to facilitate temporal integration of the pulses. The sequential modulation pulses may alternatively be temporarily contiguous relative to each other. Only one of the pulse trains may have a charge recovery pulse, in which case, the charge recovery pulse preferably has a charge approximately equal to a combined charge of the modulation pulses. In one embodiment, the plurality of pulse trains may have charge recovery pulses respectively associated with the modulation pulses, in which case, the control circuitry may be configured for controlling the modulation output circuitry in a manner that sequentially outputs the charge recovery pulses of the respective pulse trains to the common set of the electrical terminals without an intervening modulation pulse. The sequential charge recovery pulses may be temporarily spaced relative to each other, temporarily contiguous relative to each other, temporarily overlap relative to each other. In any case, the charge recovery pulses preferably have a combined charge approximately equal to a combined charge of the modulation pulses.

In one embodiment, each of the pulse trains has a fixed pulse rate less than 1.2 KHz, and the combined pulse train has an average pulse rate greater than 1.2 KHz. In another embodiment, each of the pulse trains has the same pulse rate, and the combined pulse train has a uniform pulse rate greater than the pulse rate of each of the pulse trains. An optional embodiment further comprises a user interface configured for receiving an input from a user defining a characteristic of the sequential modulation pulses, in which case, the control circuitry is configured for controlling the modulation output circuitry in a manner that sequentially outputs the modulation pulses of the respective pulse trains to the common set of the electrical terminals in accordance with the user-defined characteristic. The user interface may further be configured for receiving an input from a user specifying a set of electrodes corresponding to the common set of electrical terminal, in which case, the control circuitry is configured for selecting the common set of electrical terminals in accordance with the user-specified common set of electrodes. The neurostimulation system may further comprise a casing containing the plurality of electrical terminals, the modulation output circuitry, and the control circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 6a is timing diagram of an electrical pulse train delivered within a single timing channel of the IPG of FIG. 3 between two electrodes, wherein the interphase between biphasic pulses is relatively short;

FIG. 6b is timing diagram of an electrical pulse train delivered within a single timing channel of the IPG of FIG. 3 between two electrodes, wherein the interphase between biphasic pulses is relatively long;

FIG. 7 is a timing diagram illustrating a first technique for combining pulsed electrical waveforms delivered within four respective timing channels of the IPG of FIG. 3, wherein a combined electrical pulse train is created at a common set of electrodes;

FIG. 8 is a timing diagram illustrating a second technique for combining pulsed electrical waveforms delivered within four respective timing channels of the IPG of FIG. 3, wherein a combined electrical pulse train is created at a common set of electrodes;

FIG. 9 is a timing diagram illustrating a third technique for combining pulsed electrical waveforms delivered within four respective timing channels of the IPG of FIG. 3, wherein a combined electrical pulse train is created at a common set of electrodes;

DETAILED DESCRIPTION OF THE EMBODIMENTS

The description that follows relates to a spinal cord modulation (SCM) system. However, it is to be understood that while the invention lends itself well to applications in spinal cord modulation, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
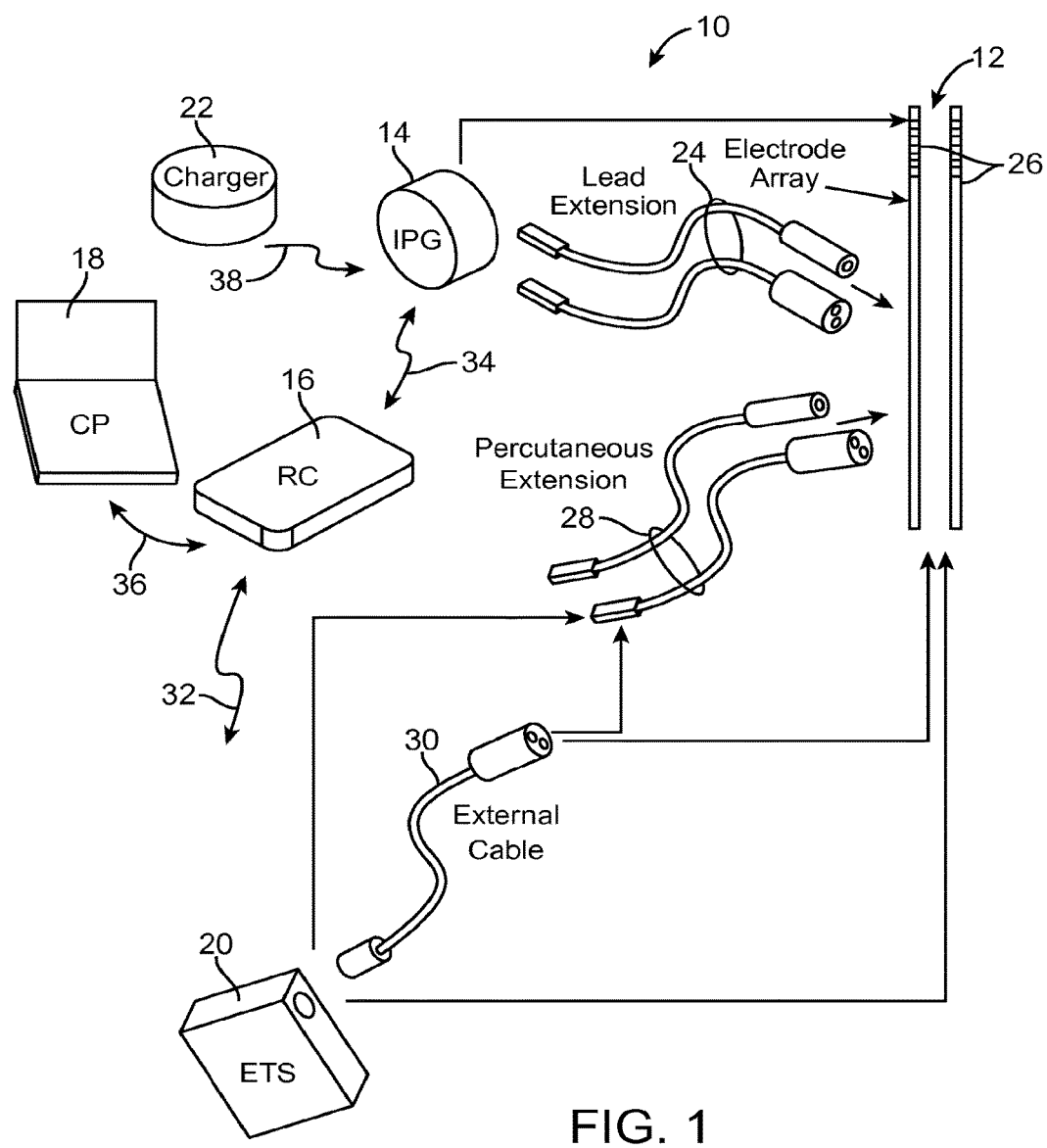
FIG. 1 is a plan view of an embodiment of a spinal cord modulation (SCM) system arranged in accordance with the present inventions.

Turning first to FIG. 1, an exemplary SCM neuromodulation system 10 generally includes one or more (in this case, two) implantable modulation leads 12, an implantable pulse generator (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 may be arranged in-line along the modulation leads 12. In alternative embodiments, the electrodes 26 may be arranged in a two-dimensional pattern on a single paddle lead. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the modulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the modulation leads 12 have been implanted and prior to implantation of the IPG 14, to test the responsiveness of the stimulation that is to be provided. Thus, any functions described herein with respect to the IPG 14 can likewise be performed with respect to the ETM 20.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
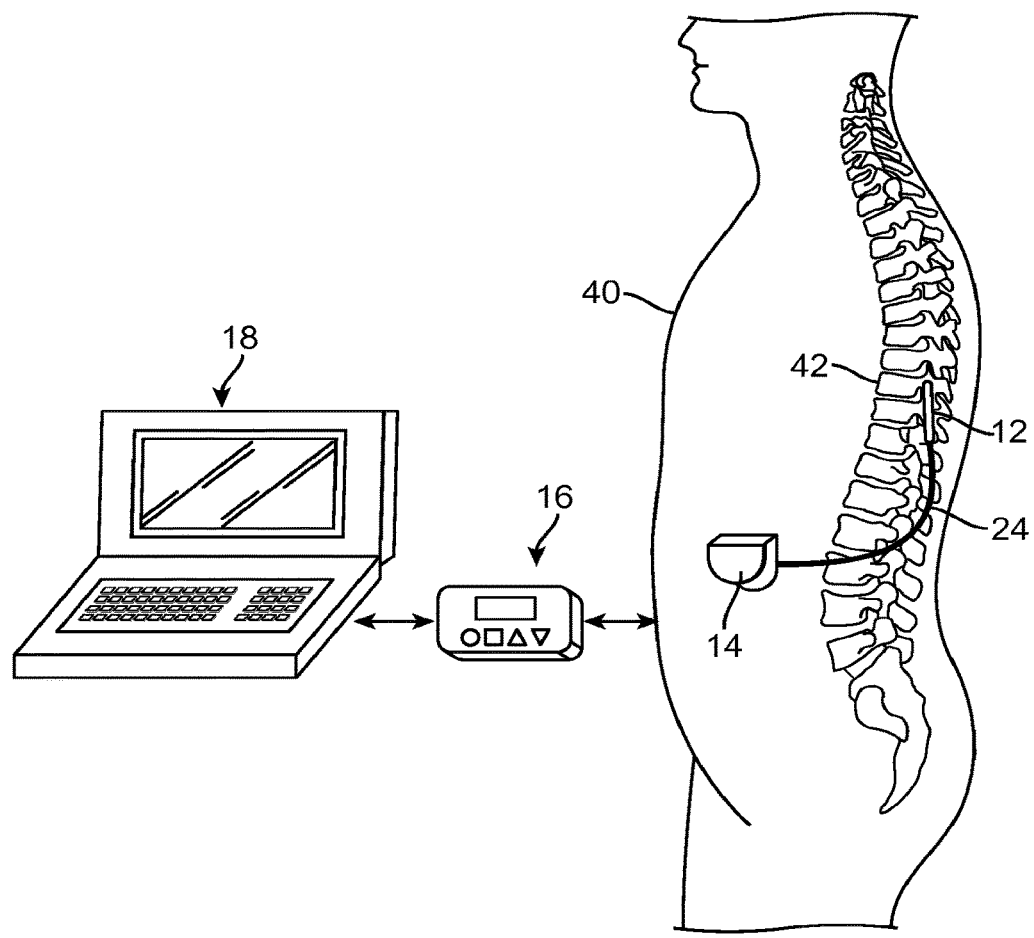
FIG. 2 is a plan view of the SCM system of FIG. 1 in use with a patient.

As shown in FIG. 2, the modulation leads (or lead) 12 are implanted within the spinal column 42 of a patient 40. The preferred placement of the modulation leads 12 is adjacent, i.e., resting near, or upon the dura, adjacent to the spinal cord area to be stimulated. The neuromodulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the modulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
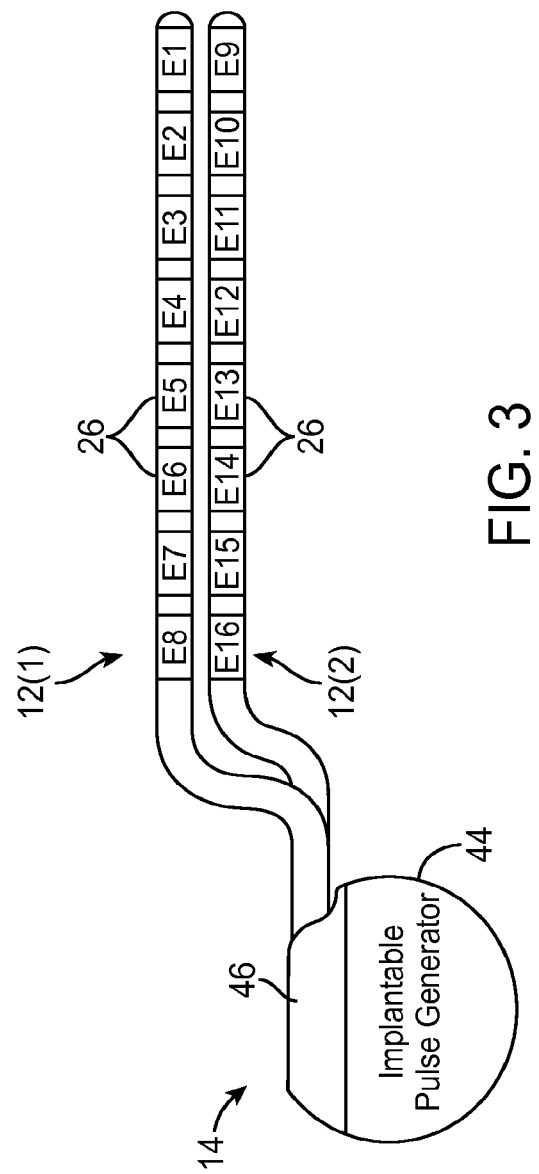
FIG. 3 is a profile view of an implantable pulse generator (IPG) and percutaneous leads used in the SCM system of FIG. 1.

Referring now to FIG. 3, the features of the modulation leads 12 and the IPG 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the modulation leads 12 mates in a manner that electrically couples the electrodes 26 to the electronics within the outer case 40. The outer case 44 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes a battery and pulse generation circuitry that delivers the electrical modulation energy in the form of one or more electrical pulse trains to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the modulation on duration X and modulation off duration Y).

Figure 4:
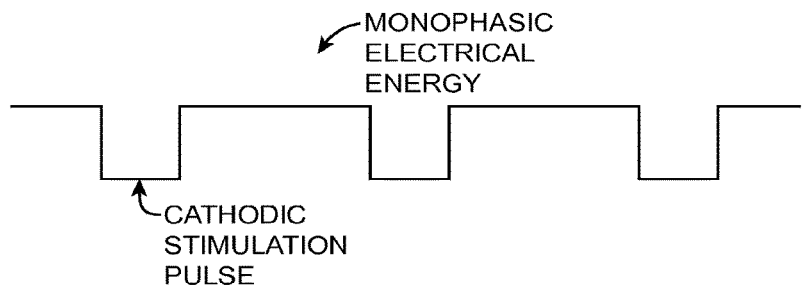
FIG. 4 is a plot of monophasic cathodic electrical modulation energy.

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12(1) may be activated as an anode at the same time that electrode E11 on the second lead 12(1) is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
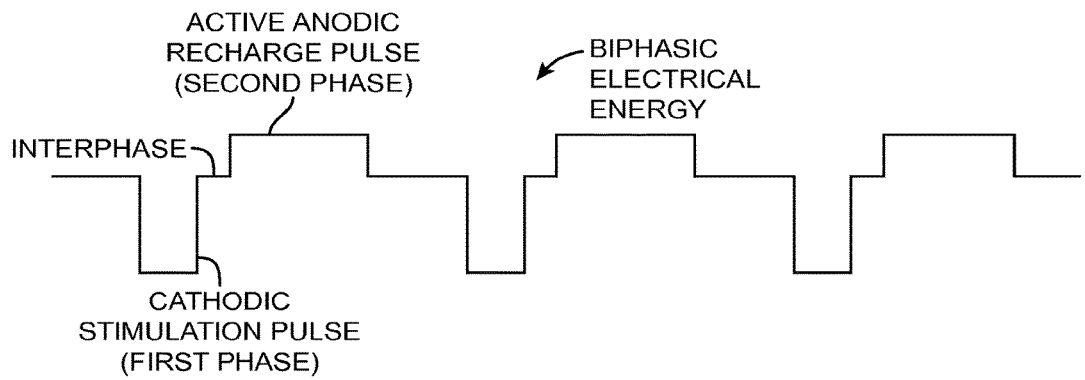
FIG. 5a is a plot of biphasic electrical modulation energy having a cathodic modulation pulse and an active charge recovery pulse.
Figure 5B:
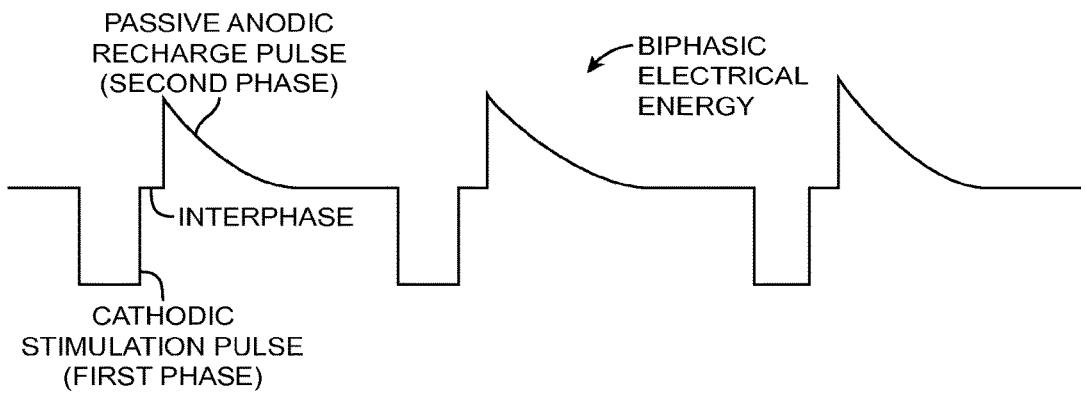
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, and a passive charge recovery pulse, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

The SCM system 10 is capable of varying the interphase of multiphasic pulses to provide different therapeutic results. For example, as illustrated in FIGS. 6a and 6b, multiphasic electrical energy takes the form an electrical pulse train 50 consisting of a plurality of biphasic pulses 52, which is delivered in a single timing channel T to a set of electrodes, and in this case, to electrode E1. As is conventional, each of the biphasic pulses 52 includes a cathodic (negative) modulation pulse (during a first phase) 54, an anodic (positive) charge recovery pulse (during a second phase) 56, and an interphase 58 between the modulation pulse 54 and charge recovery pulse 56. In the illustrated embodiment, the charge recovery pulse 56 is active. The multiphasic electrical energy is conveyed from another set of electrodes, and in this case, from electrode E2, and thus, the electrical pulse train is mirrored onto electrode E2.

As shown in FIG. 6a, the interphase 58 of each of the biphasic pulses 52 is relatively short to facilitate temporal integration between the two phases of each biphasic pulse 52. As shown in FIG. 6b, the interphase 58 of each of the biphasic pulses 52 is relatively long, so that there is minimal or no temporal integration effect between the two phases of each biphasic pulse 52.

Significant to the present inventions, the SCM system 10 is capable of concurrently delivering a plurality of individual electrical pulse trains through a respective plurality of timing channels to a common set of electrode, thereby creating a combined electrical pulse train at the common electrode set. For the purposes of this specification, electrical pulse trains are concurrently conveyed if any of their pulses overlap or are interleaved relative to each other. In a preferred method, the individual pulse trains are respectively conveyed from the plurality of electrodes to the common electrode (or electrodes) via tissue of the patient. Preferably, the tissue adjacent the common electrode (or electrodes) is therapeutically modulated (e.g., stimulated) by the combined electrical pulse train to provide the therapy. Advantageously, using multiple timing channels to combine electrical pulse trains into a single electrical pulse train at a common set of electrodes enables the SCM system 10 to create an electrical pulse train that may not otherwise be able to be created using a single timing channel due to hardware limitations in the SCM system 10.

To facilitate the combining of the individual electrical pulse trains into a single electrical pulse train at a common set of electrodes, the SCM system 10 is capable of adjusting the interphase of the multiphasic pulses in at least one of the individual electrical pulse trains. In one advantageous technique, individual electrical pulse trains are combined to create an electrical pulse train consisting of composite modulation pulses and/or composite charge recovery pulses.

For example, as shown in FIG. 7, four individual electrical pulse trains 60a-60d are respectively delivered in four timing channels T1-T4 to a common electrode set (e.g., electrode E1) to create a single combined electrical pulse train 60 at the common electrode set. In the illustrated embodiment, the single combined electrical pulse train 60 includes a series of composite modulation pulses 62, each of which is created by sequentially delivering modulation pulses 62a-62d of the respective individual electrical pulse trains 60a-60d to the common electrode set without any intervening charge recovery pulse. In the embodiment illustrated in FIG. 7, the modulation pulses 62a-62d are temporarily spaced apart from each other, such that there is a temporal integration of the modulation effects induced by the modulation pulses 62a-62d within the neural tissue's responsive time frame. To this end, each spacing between adjacent ones of the modulation pulses 62a-62d is preferably less than 1 ms. In the illustrated embodiment, the amplitude and/or width of the modulation pulses 62a-62d differ from each other. In particular, the amplitudes of the modulation pulses 62a-62d gradually increase, with the width of the modulation pulse 62a being greater than the widths of the remaining modulation pulses 62b-62d. Thus, these characteristics are reflected in the pulses 62a-62d of the resulting composite pulse 62. The amplitude and pulse width can be variable for any timing channel in order to create any desired pulse shape.

One of the electrical pulse trains 60a-60d, and in the illustrated embodiment, the electrical pulse train 60a associated within timing channel T1 is used to deliver a charge recovery pulse 64 after the delivery of sequential modulation pulses 62a-62d. Alternatively, any one of the other electrical pulse trains 60b-60d respectively associated with the timing channels T2-T4 can be selected to include the charge recovery pulse 64. In any event, the resulting electrical pulse train 60 includes this charge recovery pulse 64, which is disposed between adjacent composite modulation pulses 62. The charge recovery pulse 64 preferably includes a charge having a magnitude approximately equal to the magnitude of the combined charge of the four preceding modulation pulses 62a-62d. In effect, the composite pulse 62 and associated charge recovery pulse 64 of the combined electrical pulse train 60 form a biphasic pulse.

Although the charge recovery pulse 64 illustrated in FIG. 7 is passive, active charge recovery pulse may alternatively be used. For example, as illustrated in FIG. 8, the individual electrical pulse trains 60a-60d associated with the timing channels T1-T4 respectively include active charge recovery pulses 64a-64d that are concurrently delivered to the common electrode set subsequent to the modulation pulses 62a-62d. As a result, the combined electrical pulse train 60 at the common electrode set includes a composite charge recovery pulse 64. The magnitude of the charge of the charge recovery pulse 64 will therefore be equal to the combined charge of the four preceding modulation pulses 62a-62d. In effect, the modulation pulses 62a-62d and associated charge recovery pulse 64a-64d for the individual electrical pulse trains 60a-60d constitute symmetrical biphasic pulses, while the composite modulation pulse 62 and composite charge recovery pulse 64 of the composite electrical pulse train 60 constitute an asymmetrical bi-phasic pulse.

Like the modulation pulses 62a-62d, the amplitudes of the charge recovery pulses 64a-64d gradually increase, with the width of the charge recovery pulse 62a being greater than the widths of the remaining charge recovery pulses 64b-64d. Because the modulation pulses 62a-62d are sequentially delivered to the common electrode set, while the charge recovery pulses 64a-64d are concurrently delivered to the common electrode set, interphases 66a-66d respectively between the modulation pulses 62a-62d and charge recovery pulses 64a-64d gradually decreases.

Although the charge recovery pulses 64a-64d illustrated in FIG. 8 are concurrently delivered to the common electrode set, the charge recovery pulses 64a-64d may be sequentially delivered to the common electrode set much like the modulation pulses 62a-62d are sequentially delivered to the common electrode set, as illustrated in FIG. 9. As a result, the composite charge recovery pulse 64 of the combined electrical pulse train 60 at the common electrode set has spaced apart pulses 64a-64d. In effect, the composite modulation pulse 62 and composite charge recovery pulse 64 of the combined electrical pulse train 60 constitute a symmetrical or mirrored bi-phasic pulse. It should be noted that the individual charge recovery pulses of all four channels can be reorganized, so that the composite modulation pulses and composite charge recovery pulses both have increasing amplitude or decreasing amplitude. Although the individual timing channel may not be charge balanced in these cases, the composite pulses will be charge balanced, since they are delivered to the common electrode set.

Figure 10:
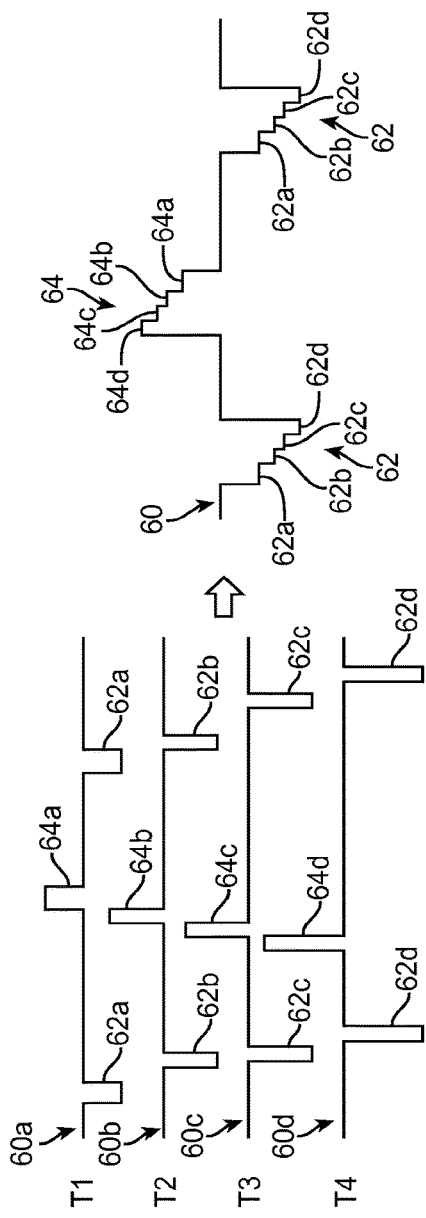
FIG. 10 is a timing diagram illustrating a fourth technique for combining pulsed electrical waveforms delivered within four respective timing channels of the IPG of FIG. 3, wherein a combined electrical pulse train is created at a common set of electrodes.

Although the modulation pulses 62a-64d and charge recovery pulses 64a-64d in the embodiment of FIG. 9 are delivered in a manner, such that the pulses of the composite modulation pulse 62 and charge recovery pulse 64 are spaced apart relative to each other, the modulation pulses 62a-64d and charge recovery pulses 64a-64d can be delivered in a manner, such that the pulses of the composite modulation pulse 62 and charge recovery pulse 64 are contiguous relative to each other, as shown in FIG. 10.

Figure 11:
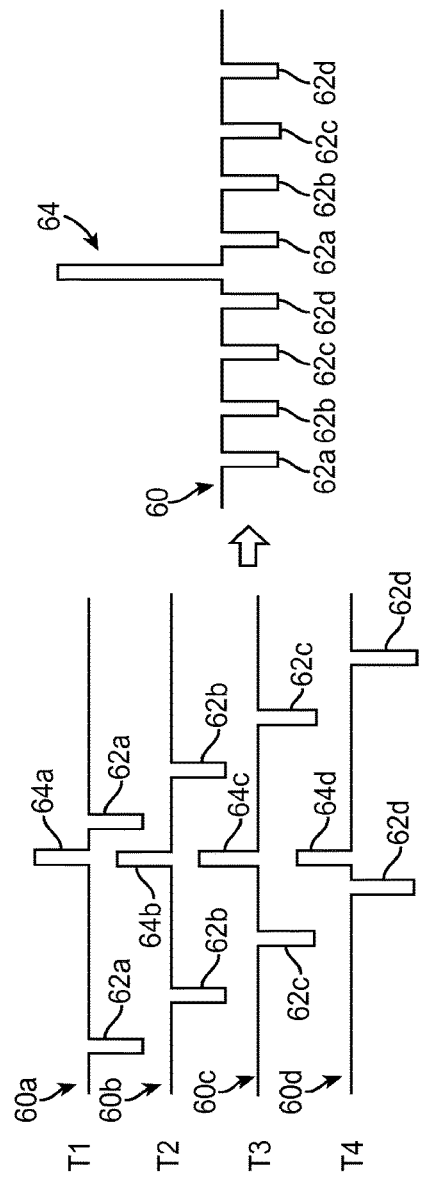
FIG. 11 is a timing diagram illustrating a fifth technique for combining pulsed electrical waveforms delivered within four respective timing channels of the IPG of FIG. 3, wherein a combined electrical pulse train is created at a common set of electrodes.

In another advantageous technique, individual electrical pulse trains having fixed pulse rates are combined to create an electrical pulse train having an average pulse rate greater than any of the fixed pulse rates of the individual electrical pulse trains. For example, as shown in FIG. 11, the four individual electrical pulse trains 60a-60d are respectively delivered in four timing channels T1-T4 to a common electrode set (e.g., electrode E1) to create a single combined electrical pulse train 60 at the common electrode set. Like the embodiments in FIGS. 7-10, the single combined electrical pulse train 60 includes a series of composite modulation pulses 62, each of which is created by sequentially delivering modulation pulses 62a-62d of the respective individual electrical pulse trains 60a-60d to the common electrode set without any intervening charge recovery pulse. However, the modulation pulses 62a-62d are delivered in such a manner that the spacings of the modulation pulses 62 throughout the combined electrical pulse train 60 are uniform. In the illustrated embodiment, the pulse rates of the individual electrical pulse trains 60a-60d are uniform and equal to each other, and the pulse rate of the single combined electrical pulse train 60 has a pulse rate that is four times as great as the pulse rate of any of the individual pulse trains 60a-60d.

In effect, an electrical pulse train can be designed to have a pulse rate equivalent to N×the pulse rate of each individual pulse train, where N is the number of timing channels. Preferably, the pulse rates of the individual pulse trains 60a-60d are less than 1.2 KHz (e.g., 500 Hz), whereas the pulse rate of the combined pulse train 60 is greater than 1.2 KHz (e.g., 2 KHz). In the illustrated embodiment, the spacings between the modulation pulses 62 are small enough, such that there is a temporal integration of stimulation effects induced from the modulation pulses 62 within the neural tissue's responsive time frame, in effect, blocking or otherwise disrupting action potentials from being conducted within the neural tissue. In the illustrated embodiment, the size (amplitude and width) of the modulation pulses 62a-62d are uniform, although such size may differ.

Like the embodiment illustrated in FIG. 8, the individual electrical pulse trains 60a-60d associated with the timing channels T1-T4 respectively include active charge recovery pulses 64a-64d that are concurrently delivered to the common electrode set subsequent to the modulation pulses 62a-62d. As a result, the combined electrical pulse train 60 at the common electrode set includes a composite charge recovery pulse 64. The magnitude of the charge of the charge recovery pulse 64 will therefore be equal to the combined charge of the four preceding modulation pulses 62a-62d.

Figure 12:
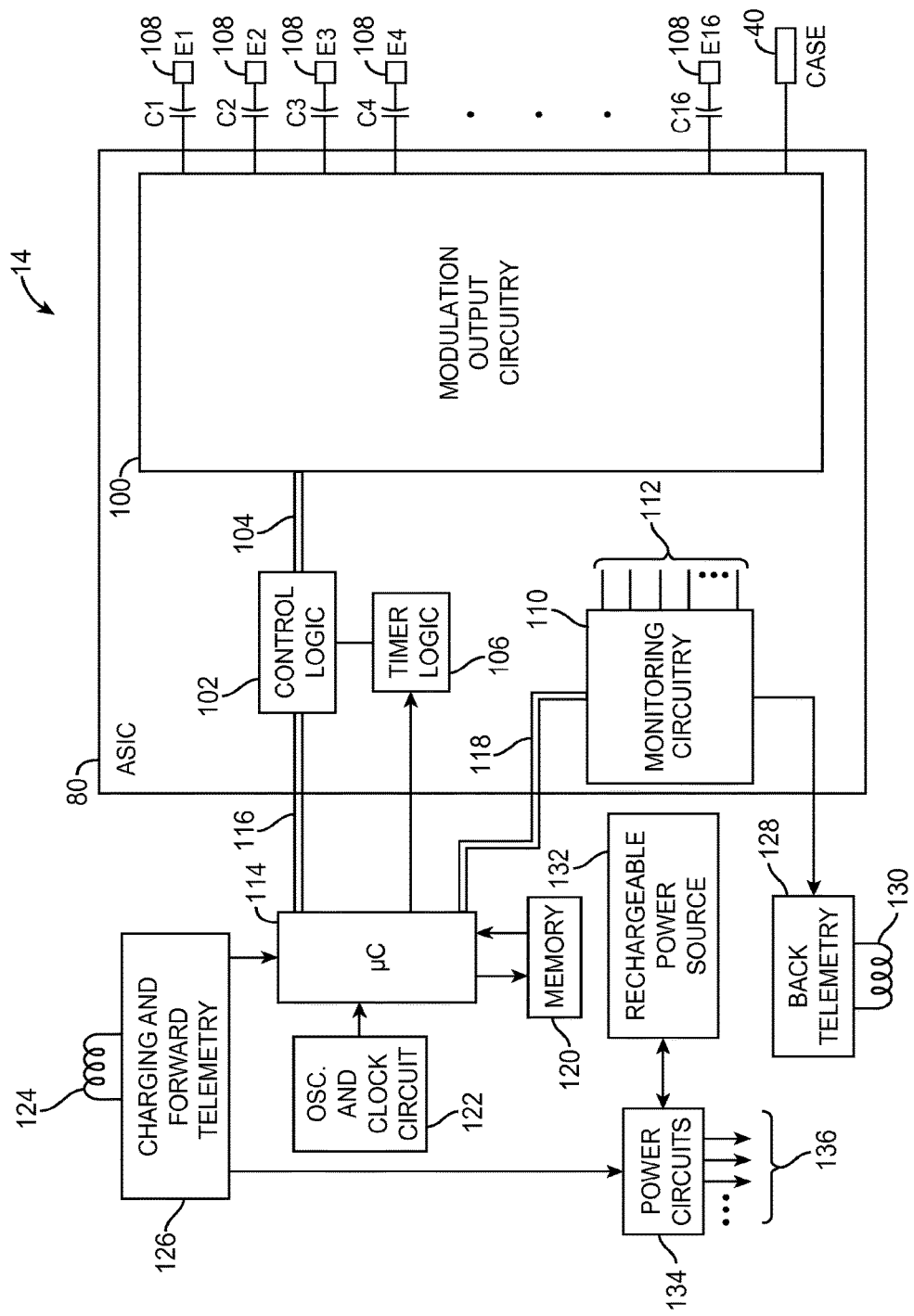
FIG. 12 is a block diagram of the internal components of the IPG of FIG. 3.

Turning next to FIG. 12, the main internal components of the IPG 14 will now be described. The IPG 14 includes modulation output circuitry 100 configured for generating electrical modulation energy in accordance with a defined pulsed waveform having a specified pulse amplitude, pulse rate, pulse width, pulse shape, and burst rate under control of control logic 102 over data bus 104. Control of the pulse rate and pulse width of the electrical waveform is facilitated by timer logic circuitry 106, which may have a suitable resolution, e.g., 10 µs. The modulation energy generated by the modulation output circuitry 100 is output via capacitors C1-C16 to electrical terminals 108 corresponding to the electrodes 26. The analog output circuitry 100 may either comprise independently controlled current sources for providing modulation pulses of a specified and known amperage to or from the electrodes 26, or independently controlled voltage sources for providing modulation pulses of a specified and known voltage at the electrodes 26.

Any of the N electrodes may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set modulation parameters including electrode polarity, amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (p). Similarly, the pulse rate is preferably adjustable within acceptable limits, e.g., from 0 to 1000 pulses per second (pps). Other programmable features can include slow start/end ramping, burst modulation cycling (on for X time, off for Y time), interphase, and open or closed loop sensing modes.

The operation of this analog output circuitry 100, including alternative embodiments of suitable output circuitry for performing the same function of generating modulation pulses of a prescribed amplitude and duration, is described more fully in U.S. Pat. Nos. 6,516,227 and 6,993,384, which are expressly incorporated herein by reference.

The IPG 14 further comprises monitoring circuitry 110 for monitoring the status of various nodes or other points 112 throughout the IPG 14, e.g., power supply voltages, temperature, battery voltage, and the like. The IPG 14 further comprises processing circuitry in the form of a microcontroller (μC) 114 that controls the control logic over data bus 116, and obtains status data from the monitoring circuitry 110 via data bus 118. The IPG 14 additionally controls the timer logic 106. The IPG 14 further comprises memory 120 and oscillator and clock circuitry 122 coupled to the microcontroller 114. The microcontroller 114, in combination with the memory 120 and oscillator and clock circuitry 122, thus comprise a microprocessor system that carries out a program function in accordance with a suitable program stored in the memory 118. Alternatively, for some applications, the function provided by the microprocessor system may be carried out by a suitable state machine.

Thus, the microcontroller 114 generates the necessary control and status signals, which allow the microcontroller 114 to control the operation of the IPG 14 in accordance with a selected operating program and modulation parameters stored in the memory 120. In controlling the operation of the IPG 14, the microcontroller 114 is able to individually generate an electrical pulse train at the electrodes 26 using the modulation output circuitry 100, in combination with the control logic 102 and timer logic 106, thereby allowing each electrode 26 to be paired or grouped with other electrodes 26, including the monopolar case electrode. In accordance with modulation parameters stored within the memory 118, the microcontroller 114 may control the polarity, amplitude, rate, pulse duration and timing channel through which the modulation pulses are provided.

Thus, it can be appreciated that, under control of the microcontroller 114, the modulation output circuitry 100 is configured for outputting a k number of individual electrical pulse trains respectively in a k number of timing channels to the electrical terminals 108, with each electrical pulse train including bi-phasic pulses as shown in FIGS. 5a and 5b. In the IPG 14, up to four stimulation programs may be stored in the memory 120, with each stimulation program having four timing channels. Thus, each modulation program defines four sets of modulation parameters for four respective timing channels. Of course, the IPG 14 may have less or more than four modulation programs, and less or more than four timing channels for each modulation program. Significantly, the microcontroller 114 may control the modulation output circuitry 100 in a manner that delivers multiple electrical pulse trains to a common set of the electrical terminals 108 (and thus, a common set of electrodes 26) to create a single electrical pulse train at the common set of electrical terminals 108; for example, in the manner described in the techniques illustrated in FIGS. 6-11. Because the functions of the microcontroller 114 can be implemented in software, these techniques can be more easily implemented within the IPG 14 without modifying pre-existing hardware designs.

The IPG 14 further comprises an alternating current (AC) receiving coil 124 for receiving programming data (e.g., the operating program and/or modulation parameters) from the RC 16 (shown in FIG. 2) in an appropriate modulated carrier signal, and charging and forward telemetry circuitry 126 for demodulating the carrier signal it receives through the AC receiving coil 124 to recover the programming data, which programming data is then stored within the memory 120, or within other memory elements (not shown) distributed throughout the IPG 14.

The IPG 14 further comprises back telemetry circuitry 128 and an alternating current (AC) transmission coil 130 for sending informational data sensed through the monitoring circuitry 110 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 120 to be downloaded from the IPG 14 to the RC 16, which information can be used to track the physical activity of the patient.

The IPG 14 further comprises a rechargeable power source 132 and power circuits 134 for providing the operating power to the IPG 14. The rechargeable power source 132 may, e.g., comprise a lithium-ion or lithium-ion polymer battery. The rechargeable battery 132 provides an unregulated voltage to the power circuits 134. The power circuits 134, in turn, generate the various voltages 136, some of which are regulated and some of which are not, as needed by the various circuits located within the IPG 14. The rechargeable power source 132 is recharged using rectified AC power (or DC power converted from AC power through other means, e.g., efficient AC-to-DC converter circuits, also known as "inverter circuits") received by the AC receiving coil 134. To recharge the power source 132, an external charger (not shown), which generates the AC magnetic field, is placed against, or otherwise adjacent, to the patient's skin over the implanted IPG 14. The AC magnetic field emitted by the external charger induces AC currents in the AC receiving coil 134. The charging and forward telemetry circuitry 136 rectifies the AC current to produce DC current, which is used to charge the power source 132. While the AC receiving coil 134 is described as being used for both wirelessly receiving communications (e.g., programming and control data) and charging energy from the external device, it should be appreciated that the AC receiving coil 134 can be arranged as a dedicated charging coil, while another coil, such as coil 130, can be used for bi-directional telemetry.

It should be noted that the diagram of FIG. 12 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-stimulator (not shown) connected to the modulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

As briefly discussed above, the RC 16 and/or CP 18 includes a user interface configured for receiving input from a user to specify the modulation parameters, including the particular electrodes 26 between which the electrical pulse trains are to be delivered. In one embodiment, composite pulses, such as those described with respect to FIGS. 7-10, can be specified by the user. For example, the user interface may present different composite pulses to the user from which to select one, after which the microcontroller 114 will automatically vary the interphases (if necessary) of the individual pulse trains, and deliver them through the timing channels in a manner that creates a combined pulse train that includes the selected complex pulse. Alternatively or optionally, the user interface allows the user to specifically define the interphases of the individual pulse trains, and combine them to create a pulse train with a user-defined complex pulse.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system, comprising:
a plurality of electrical terminals configured to be electrically connected to a plurality of electrodes, respectively;
output circuitry having at least two channels electrically connecting the output circuitry to at least one common electrical terminal from the plurality of electrical terminals, the output circuitry configured to output a first electrical waveform through a first one of the at least two channels to the at least one common electrical terminal and a second electrical waveform through a second one of the least two channels to the at least one common electrical terminal, wherein each of the first and second electrical waveforms has a stimulation phase and at least one of the first and second electrical waveforms has a charge recovery phase;
control circuitry configured to control the output circuitry to combine the first and second electrical waveforms into a combined waveform at the at least one common electrical terminal, the combined waveform having a composite characteristic that is different from characteristics in either of the first and second electrical waveforms, wherein the control circuitry is configured to combine the stimulation phases of the first and second electrical waveforms without an intervening charge recovery pulse and subsequently output the charge recovery phase to the at least one common electrical terminal; and
a user interface configured to present a selection input for use by a user to specify the combined waveform with the composite characteristic to be formed at the at least one common electrical terminal by combining the first and second electrical waveforms, wherein the user selects from the selection input to define the composite characteristic of the combined waveform, wherein the control circuitry is configured to automatically control the output circuitry in accordance with the user input received using the selection input to combine the first and second electrical waveforms at the at least one common terminal into the combined waveform with the user-defined composite characteristic.

2. The system of claim 1, wherein only one of the electrical waveforms has the charge recovery phase, and the charge recovery phase has a charge approximately equal to a combined charge of the stimulation phases.

3. The system of claim 1, wherein the first electrical waveform has a first charge recovery phase and the second electrical waveform has a second charge recovery phase, the control circuitry configured to control the output circuitry to combine and temporally overlap the first and second charge recovery phases at the at least one common electrical terminal after outputting both the stimulation phases of the first and second electrical waveforms to the common electrical terminal.

4. The system of claim 1, wherein the first electrical waveform has a first charge recovery phase and the second electrical waveform has a second charge recovery phase, the control circuitry configured to control the output circuitry to sequentially deliver the first and second charge recovery phases at the at least one common electrical terminal after outputting both the stimulation phases of the first and second electrical waveforms to the common electrical terminal.

5. The system of claim 4, wherein the first and second charge recovery phases are temporally spaced from each other in the combined waveform.

6. The system of claim 4, wherein the first and second charge recovery, phases are contiguous to each other in the combined waveform.

7. The system of claim 1, wherein the control circuitry is configured to control the output circuitry to sequentially deliver the stimulation phases of the first and second waveforms without the intervening charge recovery phase.

8. The system of claim 7, wherein the sequentially-delivered stimulation phases of the first and second electrical waveforms are uniformly spaced from each other in the combined waveform.

9. The system of claim 7, wherein the sequentially-delivered stimulation phases of the first and second electrical waveforms are spaced apart from each other in the combined waveform by a time period less than 1 ms.

10. The system of claim 1, wherein the control circuitry is configured to control the output circuitry to contiguously deliver the stimulation phases of the first and second waveforms without the intervening charge recovery phase.

11. The system of claim 1, wherein more than one of the electrical waveforms has charge recovery phases, and a combined charge of the charge recovery phases is approximately equal to a combined charge of the stimulation phases.

12. The system of claim 1, wherein the first electrical waveform includes a first pulsed electrical waveform.

13. The system of claim 12, wherein the second electrical waveform includes a second pulsed electrical waveform.

14. The system of claim 13, wherein each of the first and second pulsed electrical waveforms has a fixed pulse rate less than 1.2 KHz, and the combined waveform has an average pulse rate greater than 1.2 KHz.

15. The neuromodulation system of claim 13, wherein each of the first and second pulsed electrical waveforms has the same pulse rate.

16. The system of claim 1, wherein the first and second pulsed electrical waveforms include pulses with a different pulse amplitudes or different pulse widths, or both different pulse amplitudes and different pulse widths.

17. The system of claim 1, wherein the charge recovery pulse is passive.

18. The system of claim 1, wherein the charge recovery pulse is active.

19. A system, comprising:
a plurality of electrical terminals configured to be electrically connected to a plurality of electrodes, respectively;
output circuitry having a plurality of channels electrically connecting the output circuitry to at least one common electrical terminal from the plurality of electrical terminals, the output circuitry configured to output a plurality of electrical waveforms through the plurality of channels, respectively, to the at least one common electrical terminal, wherein each of the plurality of waveforms has a stimulation phase and at least one of the plurality of waveforms has a charge recovery phase;
control circuitry configured to control the output circuitry to combine the plurality of electrical waveforms into a combined waveform at the at least one common electrical terminal, the combined waveform having a composite characteristic that is different from characteristics in any of the plurality of electrical waveforms, wherein the control circuitry is configured to combine the stimulation phases of the plurality of electrical waveforms without an intervening charge recovery pulse and subsequently output the charge recovery phase to the at least one common electrical terminal; and
a user interface configured to present different waveform selections for selection by a user to specify the combined waveform with the composite characteristic to be formed at the at least one common electrical terminal by combining the first and second electrical waveforms, receive a user input selecting one of the different combined waveforms to define the composite characteristic of the combined waveform, wherein the control circuitry is configured to automatically control the output circuitry to combine the plurality of electrical waveforms at the at least one common terminal into the combined waveform with the riser-defined composite characteristic.

20. The system of claim 19, wherein the first electrical waveform has a first charge recovery phase and the second electrical waveform has a second charge recovery phase, the control circuitry configured to control the output circuitry to combine and temporally overlap the first and second charge recovery phases at the at least one common electrical terminal after outputting both the stimulation phases of the first and second electrical waveforms to the common electrical terminal.

* * * * *